United States Patent [19]

Capaccio

[11] Patent Number: 5,183,469
[45] Date of Patent: Feb. 2, 1993

[54] DEVICE FOR THE REMOVAL AND REPLACEMENT OF A NEEDLE SHIELD

[75] Inventor: Paul R. Capaccio, Clifton, N.J.

[73] Assignee: Becton, Dickinson and Company, Franklin Lakes, N.J.

[21] Appl. No.: 698,512

[22] Filed: May 10, 1991

[51] Int. Cl.⁵ .................. A61M 5/32; B65D 83/10
[52] U.S. Cl. ...................... 604/192; 206/365
[58] Field of Search ............... 206/364–367; 604/192, 263, 110, 197

[56] References Cited

U.S. PATENT DOCUMENTS

| | | | |
|---|---|---|---|
| D. 302,295 | 7/1989 | Hanifl et al. | D24/25 |
| 4,717,386 | 1/1988 | Simmons | 604/192 |
| 4,737,149 | 4/1988 | Gillilan | 604/192 |
| 4,742,910 | 5/1988 | Staebler | 206/365 |
| 4,836,373 | 6/1989 | Goldman | 206/366 |
| 4,846,803 | 7/1989 | Emerson | 604/263 |
| 4,979,945 | 12/1990 | Wade et al. | 604/192 |
| 4,986,817 | 1/1991 | Code | 604/192 |
| 5,037,400 | 8/1991 | Curry | 604/192 |
| 5,078,695 | 1/1992 | Farrar, Jr. et al. | 604/192 |
| 5,078,696 | 1/1992 | Nedbaluk | 604/192 |
| 5,102,083 | 4/1992 | Baskas | 248/223.4 |

OTHER PUBLICATIONS

Syringe Scabbard Systems Brochure, undated.

*Primary Examiner*—John D. Yasko
*Assistant Examiner*—Adam J. Cermak
*Attorney, Agent, or Firm*—John L. Voellmicke

[57] ABSTRACT

A device for the removal and replacement of a needle shield having a distal end, an open proximal end and a side wall therebetween having an outside surface includes a housing having a proximal end and a distal end. The housing includes a bore therein beginning at the proximal end. A threaded portion is provided in the housing along the bore and accessible through the bore. The threaded structure is spaced from the proximal end of the housing and is capable of engaging and holding the outside surface of a needle shield which is placed into the bore through the proximal end of the housing and rotated in a direction to advance the needle shield distally along the threaded structure.

17 Claims, 5 Drawing Sheets

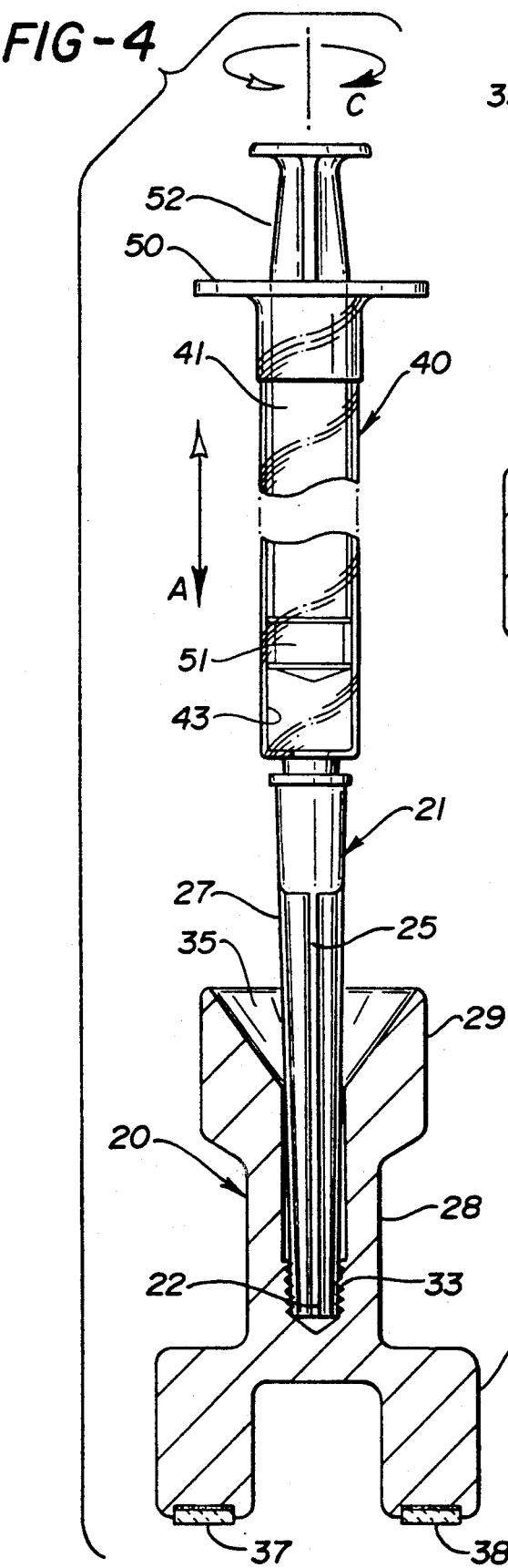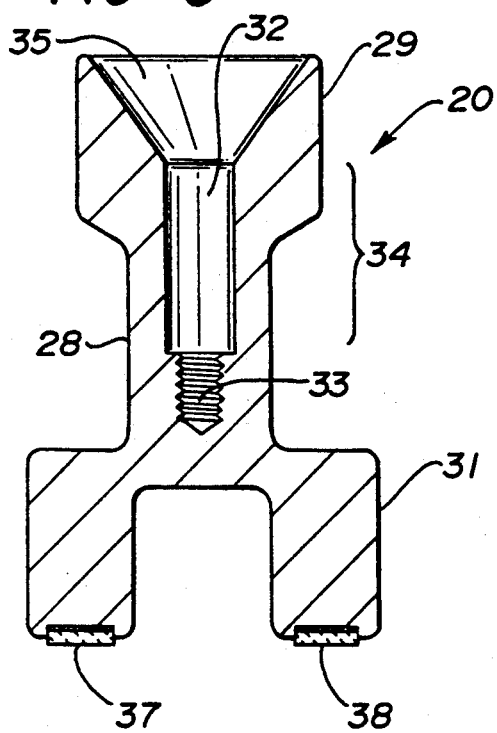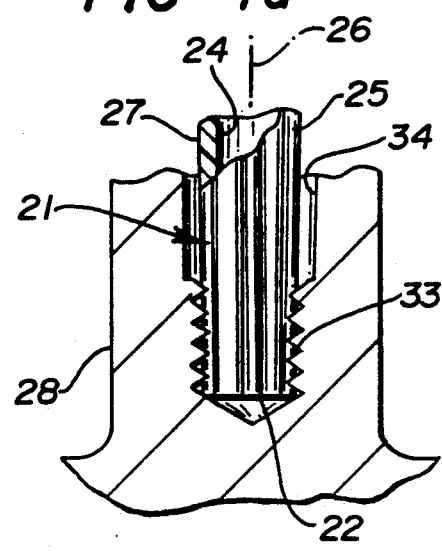

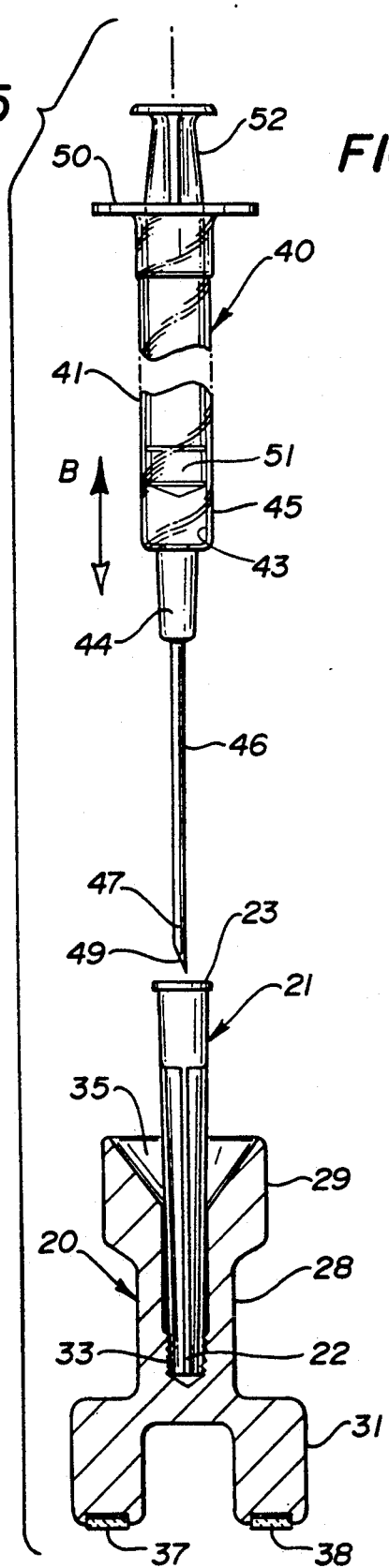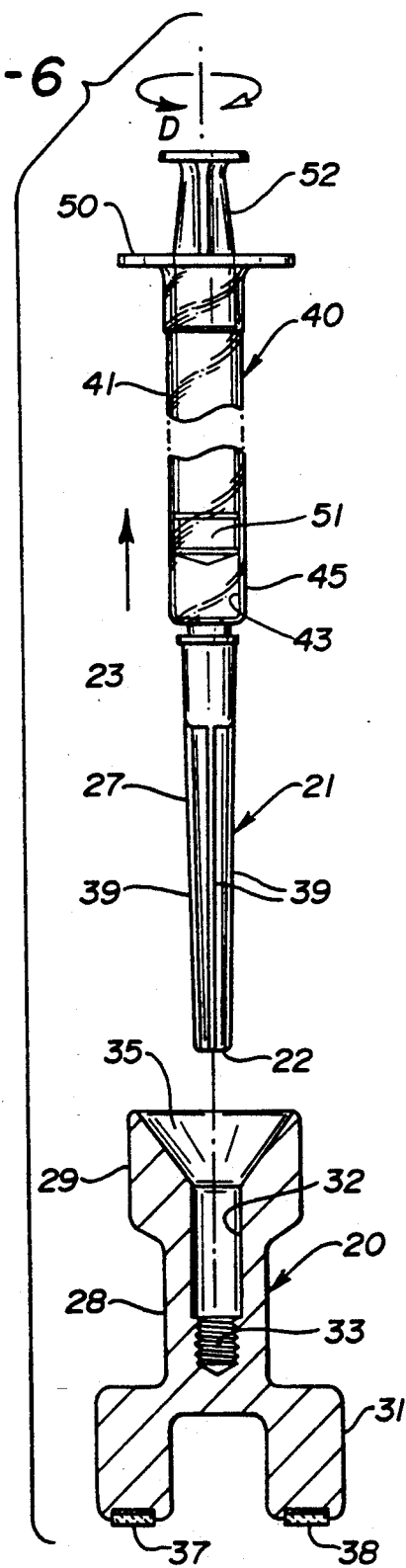

DEVICE FOR THE REMOVAL AND REPLACEMENT OF A NEEDLE SHIELD

BACKGROUND OF THE INVENTION

1. Field of the Invention

The present invention relates to needle reshielding devices and more particularly relates to a device and a method for the removal and the replacement of a needle shield.

2. Description of Related Information

Hypodermic needles are used throughout the world for numerous purposes. Most commonly, they are used in conjunction with syringes to deliver medication to a patient or to an intravenous delivery system having a pierceable entry port. Hypodermic needles are also used with syringes for taking blood samples and in conjunction with evacuated tubes for taking blood samples.

A commercially available hypodermic needle generally consists of a needle shield and a needle assembly. The needle shield has an elongate body and an open proximal end. The needle assembly includes a hub having a passageway therethrough and a needle cannula projecting outwardly from the hub and having a lumen therethrough in fluid communication with the passageway. The hub may be a separate component or an integral part of the syringe barrel. In either case the needle shield usually frictionally engages the hub which many times has a frusto-conically shaped exterior surface to frictionally engage the inside diameter of the needle shield to hold the needle shield in place over the needle thus protecting the needle from damage from outside forces and protecting the user from accidental skin puncture by the needle.

At time of use the needle shield is removed exposing the sharp distal point of the needle cannula. Even before use, the sharp point of the needle can inflict minor injury if the user inadvertently sticks himself or herself. After use the sharpened needle tip poses an additional problem because it may be contaminated and be an instrument for the inadvertent transfer of infection or disease. Many hospitals require reporting of all accidental needle sticks so that even an incident with a clean sterile needle is a reportable incident requiring expenditure of time and money.

Great effort has been expended to minimize the possibility of inadvertent needle sticks. Inadvertent needle sticks can happen during the act of reshielding as the user attempts to guide the sharp needle into the small diameter proximal opening of the needle shield so that the needle shield re-engages the hub. The user may miss the needle shield and stick his or her own hand. It is the belief of some that needle re-shielding should not be attempted and the used hypodermic needle should be disposed of immediately. In many applications this type of disposal may not be practical if the disposal apparatus or means is not in the area where the hypodermic needle is being used. Others recommend cautious re-shielding by one-handed techniques or one-handed devices or two-handed techniques using devices having projections for shielding the user's hand and/or for guiding the needle toward the needle shield interior.

U.S. Pat. No. 4,717,386 to Simmons teaches a device for uncapping and capping the protective sheath of a hypodermic needle. In one embodiment, Simmons provides a hand-held shield to isolate the fingers from the sheath and to provide a barrier to protect the user in case the needle misses the opening in the sheath upon reassembly. Reshielding devices such as these must be carefully designed and carefully used. The shield material must be strong enough to prevent the needle from penetrating all the way through to the user's hands yet not hard enough that the needle would slide off the shield into the user's hand. Although this embodiment of Simmons' device greatly reduces the chance of needle stick it does not eliminate it. Simmons teaches another embodiment which is attached to a work surface providing one-handed uncapping and re-capping. Both embodiments of Simmons appear to work by frictionally engaging the exterior of the sheath to hold the sheath with greater force than the resisting force of the sheaths frictional engagement to the tapered needle mount of the syringe.

U.S. Pat. No. 4,742,910 to Staebler also enables a needle sheath holder which can be hand-held or set in a stand or a test tube rack. The needle sheath holder frictionally engages the needle sheath through the deflection of a plurality of gripper members in a gripping assembly. It is unclear if the needle sheath can be removed from the holder by applying forces to the syringe without disengaging the needle sheath from the syringe or if Staebler intends that the needle sheath remain permanently in the holder.

U.S. Pat. No. Des. 302,295 to Hanifl et al. illustrates a needle resheather. This needle resheather appears to rely on frictional engagement with the sheath and because of its right angle structure appears to be mountable on either of its two sides or in a corner.

The needle sheath holding device of Simmons, Staebler and Hanifl et al. undesirably rely on frictional engagement of the needle sheath. Frictional engagement is not desirable because increasing the axial force on the hypodermic syringe to engage the sheath in the holder not only tightens the grip of the holder on the sheath also increases the frictional engagement force of the sheath to the needle hub. Increasing forces to engage require increasing forces to withdraw the syringe from the needle sheath which may require such an amount of force as to cause the assembly to abruptly come apart and injuring the user. It would be desirable if the forces used to engage the needle sheath into the holder did not also make it more difficult for the needle to be removed from the sheath. Also, the use for friction for engagement can result in a system which acts differently with every use. Higher engagement forces for the sheath into the holder result in higher removal forces necessary to expose the needle for use. Also final removal of the needle sheath from the holder may be difficult.

U.S. Pat. No. 4,737,149 to Gillilan also teaches a device for the removal or attachment of a needle sheath to a needle assembly using resilient material to frictionally engage the needle shield. Gillilan has an apparent advantage over other friction devices that rely on friction to hold the needle shield in that structure to assist in ejecting the needle shield from the device is taught.

U.S. Pat. No. 4,979,945 to Wade et al. teaches a syringe needle cap resheathing and removal apparatus capable of single-handed operation for three different standard needle cap shapes. The device of Wade et al. provides a lateral recess of varying shape to accept several types of needle caps and hold them in position through the shape of the side walls along the lateral recess and the cantilever flexing of one of the members to apply a frictional grip on the needle shield. In the Wade et al. device the force used to engage and remove the needle cap from the apparatus is directed perpendicularly to the axis of the needle cap.

A syringe scabbard sold by Syringe Scabbard Systems of Lyndhurst, Ohio is a device for one-handed unshielding and re-shielding which is provided with an adhesive base to adhere it to a work surface. A syringe scabbard device apparently relies on a claw-shaped lip to engage the proximal surface of the needle shield so that the syringe may be withdrawn while the needle shield is retained in the device. This device does not appear to rely on axially applied frictional forces to engage the needle shield in he device. Apparently there is enough space in the Syringe Scabbard device to allow for re-shielding and removal without engaging the lip. A device such as this may present problems in that it appears that the claw-shaped lip may also be capable of removing the hypodermic needle from syringes which do not have the locking luer feature. Also the Syringe Scabbard device does not appear to hold the needle shield after removal but just to provide a restrained storage area wherein the needle shield may move around making re-shielding a more difficult time-consuming procedure since the shield is not restrained from lateral motion.

Although the art has provided improved devices to facilitate the removal and re-engagement of needle shields while lowering the possibility of accidental needle sticks there is still a need for a simple, straight-forward, reliable, easily fabricated device for the removal and replacement of a needle shield which holds the needle shield in a releasably secure position without relying on axially applied frictional forces to engage the needle shield in the device. There is also a need for a device for the removal and replacement of a needle shield which will accommodate commercially available needle shields without alteration of the needle shields.

SUMMARY OF THE INVENTION

A device for the removal and replacement of a needle shield having a distal end, an open proximal end and a side wall therebetween having an outside surface includes a housing having a proximal end and a distal end. The housing includes a bore therein beginning at the proximal end. Thread means is provided in the housing along the bore and is accessible through the bore. The thread means is spaced from the proximal end of the housing and is capable of engaging and holding the outside surface of the needle shield which is placed into the bore through the proximal end of the housing and rotated in a direction to advance the needle shield distally along the thread means.

In accordance with another embodiment of the present invention, a device for the removal and replacement of a needle shield having a distal end, an open proximal end and a side wall therebetween having an outside surface includes a housing having a proximal end and a distal end. The housing includes a bore therein beginning at the proximal end. Thread means is provided in the housing along the bore and is accessible through the bore. The thread means is spaced from the proximal end of the housing by a first portion of the bore between the proximal end of the housing and the thread means. The thread means includes a right-hand thread which is capable of engaging the holding the outside surface of the needle shield which is placed in the bore through the proximal end of the housing and rotated in a clockwise direction. Guide means is provided for directing the distal end of the needle shield toward the bore. Stabilizing means is provided at the distal end of the housing for positioning and holding the housing for allowing a person to remove and replace a needle shield without touching the device.

In accordance with another aspect of the present invention a method for removal a needle shield having a distal end, an open proximal end and a side wall therebetween having an outside surface by using a housing having a proximal end, a distal end and a bore therein beginning at the proximal end, and including a thread means along the bore which is accessible through the bore so that the thread means is capable of engaging and holding the outside surface of the needle shield comprising: (a) directing a hypodermic syringe and needle assembly having a needle shield attached toward the housing; (b) causing the needle shield to enter the bore through the proximal end of the housing; (c) rotating the syringe so that the needle shield rotates in a direction to advance the needle shield distally along the thread means; and (d) applying an axial proximally directed force to the syringe causing the syringe and needle assembly to disengage from the needle shield while the needle shield remains held in the housing.

BRIEF DESCRIPTION OF THE DRAWINGS

FIG. 3 is a cross-sectional view of the device of FIG. 1 taken along line 3—3;

FIG. 4 is a partial cross-sectional side elevation view illustrating the device of FIG. 3 engaged with a hypodermic needle assembly including a needle shield;

FIG. 4a is an enlarged view illustrating the needle shield engaging threads of the device engaging the needle shield;

FIG. 5 is an exploded view showing the syringe and needle assembly being separated from the needle shield while the device retains the needle shield;

FIG. 6 illustrates the removal of the syringe assembly from the device after use for disposal of the syringe;

DETAILED DESCRIPTION

Figure 1:
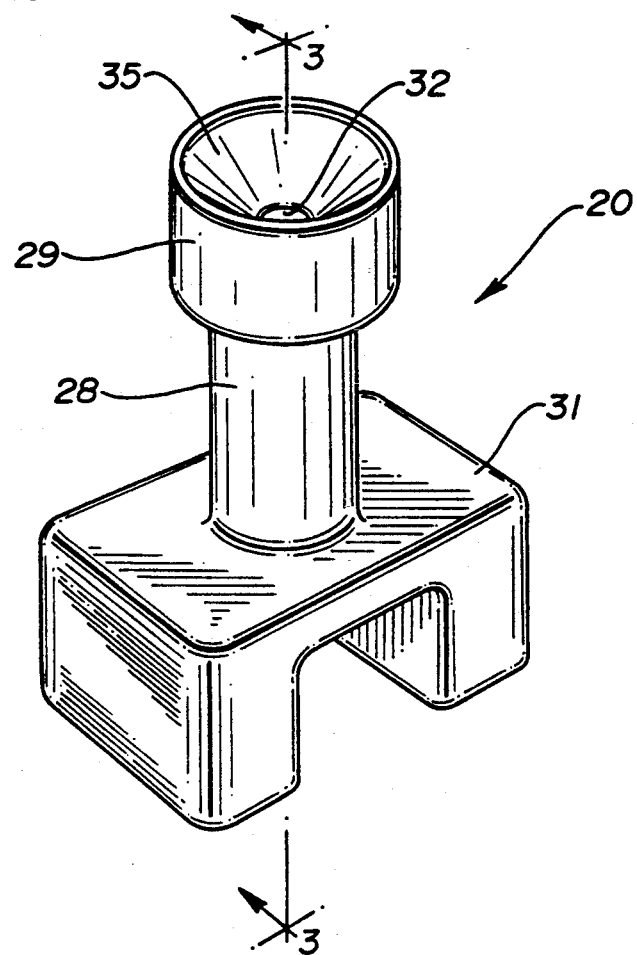
FIG. 1 is a perspective view of the device for the removal and replacement of a needle shield of the present invention.
Figure 2:
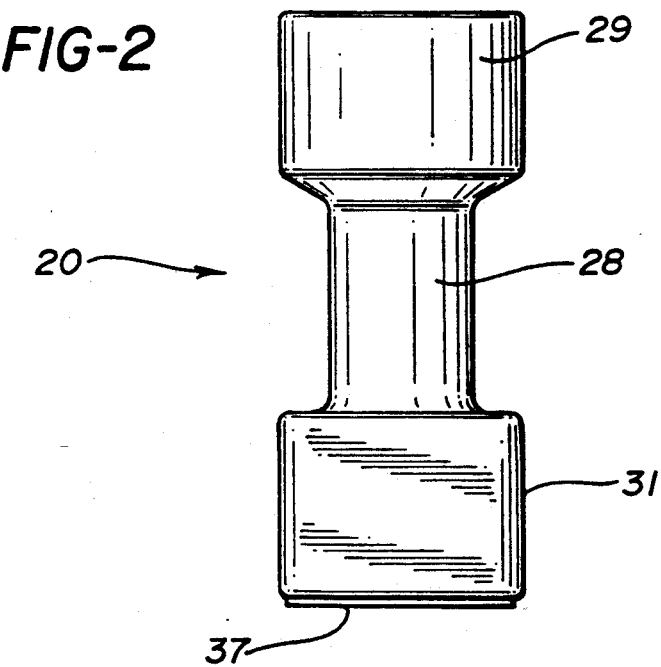
FIG. 2 is a side elevation view of the device of FIG. 1.

While this invention is satisfied by embodiments in many different forms, there is shown in the drawings and will herein be described in detail preferred embodiments of the invention with the understanding that the present disclosure is to be considered exemplary of the principles of the invention and not intended to limit the invention to the embodiments illustrated. The scope of the invention will be measured by the appended claims and their equivalents.

FIGS. 1–6 illustrate a device 20 for the removal and replacement of a needle shield 21. A typical needle shield includes a distal end 22, an open proximal end 23 and a side wall 25 therebetween having an outside surface 27.

For the purposes of the description of the present invention, the term "distal end" refers to the end furthest from the person holding the syringe, whereas the term "proximal end" refers to the end closest to the holder of the syringe.

Device 20 for the removal and replacement of a needle shield includes a housing 28 having a proximal end 29 and a distal end 31. The housing also includes bore 32 therein beginning at the proximal end.

Thread means such as screw threads 33 are positioned along said bore and accessible through said bore. The threads are spaced from proximal end 29 by a first portion 34 of the bore between the proximal end of the housing and the screw threads. The screw threads in this embodiment are right-hand machine threads capable of engaging and holding the outside surface of a plastic needle shield which is placed in bore 32 through proximal end 29 of the housing and rotated in a clockwise direction as best illustrated in FIGS. 4 and 4a.

Outside surface 27 of the side wall of the needle shield is illustrated with ribs 39 which are engaged by the screw threads in the housing to hold the needle shield in the housing as will be explained in more detail hereinafter. The threads of the present invention work equally well with numerous plastic needle shields including needle shields that are substantially circular outside surfaces and the needle shield embodiment illustrated here and is merely representative of the many commercially available plastic needle shields.

Guide means such as frusto-conically shaped guide surface 35 is provided to direct distal end 22 of needle shield 21 toward and into bore 32.

Device 20 also preferably includes stabilizing means at distal end 31 of the housing for positioning and holding the housing and allowing a person to remove and replace a needle shield without touching the device. In this embodiment stabilizing means includes magnets 37 and 38 for removably attaching the device to ferro-magnetic metal surfaces such as desk tops and sheet metal walls, including cabinet walls, for convenient positioning of the device in an area close to the point of use of the syringe.

The instant invention may be used with a wide variety of devices having a needle assembly and a needle shield wherein the needle shield is associated with the cannula mounting structure of the needle assembly via frictional interference fit or other structural relationship which allows the removal of the needle shield by the application of axial force. Such devices are extensively available for numerous uses such as pharmacy prefilling programs, blood sampling, medication delivery, I.V. therapy devices and the like. The disposable hypodermic syringe and needle assembly described herein for use with the instant invention is representative of these many devices.

Generally speaking, the hypodermic syringe and needle assembly 40 consists of a cylindrical barrel 41 having a chamber 43 for retaining fluid and a frustoconically shaped tip portion 44 extending from a distal end 45 of the barrel having a passageway therethrough communicating with the chamber. A needle cannula 46 having a distal end 47 and a sharpened point 49 extends outwardly from tip portion 44. The needle cannula includes a lumen therethrough in fluid communication with the passageway and chamber 43. A stopper 51 is slidably positioned in fluid-tight engagement inside the barrel and is connected to rigid plunger rod 52 to facilitate its operation. The plunger rod is accessible outside of open proximal end 50 of the barrel and is provided to move the stopper along the barrel to force fluid into and out of the chamber through the passageway and the lumen of the needle cannula. The operation of syringes is well known in the art.

The removable needle shield is also provided to protect the needle from damage before use and to protect the user from accidental needle sticks. Needle shields are usually made of plastic and include distal end 22, open proximal end 21 and a side wall 25 therebetween defining a longitudinal axis 26. The side wall includes outside surface 27 which may be smooth and cylindrically shaped. The outside surface of the needle shield may also contain longitudinal ribs. Some needle shields have a threaded portion on the outside surface at the distal end. The threaded portion of this type of needle shield is usually provided when the needle shield will also act as a plunger rod by engaging complimentary female threads in the syringe stopper.

Needle shield 21 is removably engaged with tip portion 44 of the syringe barrel through a frictional interference fit between the outside surface of the tip portion and an inside surface 24 of side wall 25 at the proximal end of the needle shield. Because tip portion 44 of barrel 40 is frusto-conically shaped, the engagement of the needle shield and the tip portion can vary from weak to very strong depending on the amount of force used to force the parts together. The more force that is used to join the needle shield and the tip portion, the more force that will be needed to separate these components.

Many syringe and needle assemblies include a separate needle hub connected to the needle cannula. The needle hub includes a frusto-conical conically shaped inside surface which frictionally engages the tip portion of the barrel. The hub also includes a frusto-conically shaped exterior surface or structure which frictionally engages the needle shield just as the syringe barrel tip engages the needle shield in the example syringe described hereinabove. The subject invention works with both types of syringe needle assemblies and the embodiment described hereinabove and in FIGS. 1–6 is merely representative of the many syringe and needle assemblies available having a removably engaged needle shield.

In use, the device of the instant invention is positioned on a work surface such as a tabletop. In the instant embodiment wherein stabilizing means includes magnets 37 and 38 it is desirable to have a tabletop made of ferro-magnetic material so that the device firmly attaches itself to the work surface. Other equally desirable forms of attachment means will be described hereinafter. To remove the needle shield the user directs a syringe and needle assembly 40 with needle shield 21 attached toward housing 28 in direction A as illustrated in FIG. 4. The user causes needle shield 21 to enter bore 32 through proximal end 29 of the housing, until the needle shield contacts right-hand screw threads 33.

The user then rotates the syringe so that the needle shield rotates in a direction to advance the needle shield distally along the threads. In this embodiment, rotation in direction C, as illustrated in FIG. 4, will engage the needle shield with the threads of the device. The relationship between the needle shield and the threads is shown more clearly in FIG. 4a. It is desirable to have the threads made of a material which is harder than the needle shield such as metal, a metal-plated or coated substrate, a metal thread insert or another material, such as a plastic which is harder than the needle shield. Threads 33 engage and deflect the surface of the needle shield to make relative motion between the device and the needle shield in a direction along the axis of the needle shield very difficult.

The user now applies an axial proximally directed force B, to syringe and needle assembly 40, as illustrated in in FIG. 5, causing syringe and needle assembly 40 to disengage from needle shield 21 which remains securely held by device 20. The user may now, following safe procedure, use the syringe to perform a specific task such as delivery of medication to a patient. After the syringe is used for this purpose, the needle tip is no longer sterile and may present a hazard to the user while it remains unshielded. To re-shield as best illustrated in FIGS. 5-6, the user directs syringe and needle assembly 40 toward needle shield 21 and housing 28 causing the syringe and needle assembly to frictionally engage the needle shield. The user now rotates the syringe and needle assembly which is attached to the needle shield in a direction to move the needle shield proximally along the threads until the threads no longer engage the outside surface of the needle shield. In this embodiment, the direction of a rotation to disengage the needle shield is counter-clockwise and is indicated by the letter D in FIG. 6.

The device of the instant invention works more smoothly and feels more consistent from needle shield to needle shield if the user makes an effort to align longitudinal axis 26 of the needle shield with the longitudinal axis of that portion of bore 32 containing screw threads 33. In order to make this alignment automatic, and remove the burden from the user, first portion 34 of the bore is provided. This portion of the bore located proximally from the threads causes the needle shield axis to align itself with the thread at longitudinal axis 40 and is a preferred, but not a necessary, element of the instant invention.

In order to guide the needle shield into the bore a guide means such as frusto-conically shaped guide surface 35 is provided. A guide means is preferred, but not necessary, for the instant invention. The guide means is particularly useful if the diameter of the first portion of the bore is close to the outside diameter of the needle shield. The closer the diameter of the bore is to the needle shield outside diameter the more useful the guide surface is in smoothly positioning the needle shield for entering into the bore.

It can be seen that device 20 provides a safe and convenient way to remove and replace a needle shield from a syringe and needle assembly or the like. An important feature of the instant invention is that it does not rely on axially applied frictional forces to hold the needle shield in the device. As has been noted hereinabove, increasing force used to engage a needle shield in a holder which relies on friction will also increase the frictional engagement of the needle shield to the syringe and needle assembly. Accordingly, the force required to remove the syringe and needle assembly from the needle shield may be excessive or so abrupt as to cause injury to the user. In the instant invention, the forces exerted to join the device and the needle shield are substantially in a plane perpendicular to the longitudinal axis of the needle shield and do not as directly affect the strength of the attachment between the needle shield and the syringe and needle assembly.

FIGS. 7-11 illustrate alternative embodiments and features of the present invention. The structure of these alternative embodiments are similar to the embodiment of FIGS. 1-6. Accordingly, substantially similar components that perform substantially similar functions will be numbered identically to those components of the embodiment of FIGS. 1-6 except a suffix such as "a" "b" "c" or "d" will be used to identify these components in FIGS. 7-11.

Figure 7:
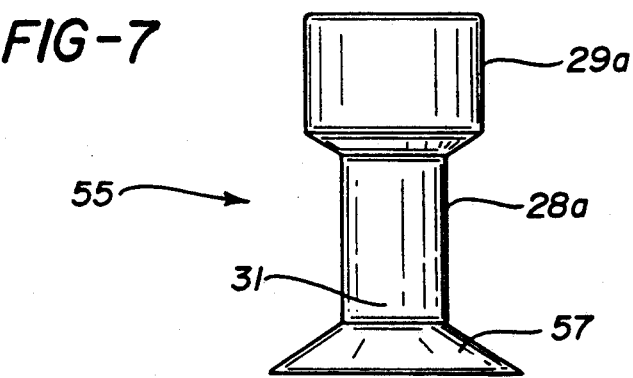
FIG. 7 is a side elevational view of an alternate embodiment of the device of the present invention having a suction cup mounting structure at the distal end.

Referring now to FIG. 7, an alternative embodiment of a device 55 for the removal and replacement of a needle shield (not shown) includes a housing 28a having a proximal end 29a and a distal end 31a. The housing includes a bore (not shown) beginning at said proximal end. Thread means such as a right-handed or left-handed machine thread of single or multiple pitch is included in said housing along the bore and accessible through the bore. The thread means is capable of engaging holding the outside surface of a needle shield which is placed into the bore through the proximal end of the housing and rotated in a direction to advance the needle shield distally along the thread means. A stabilizing means in the form of a suction cup 57 is provided at distal end 31a of the housing for positioning and holding the housing and for allowing a person to remove and replace the needle shield without touching device 55. Suction cup 57 is suitable for attaching the device of the present invention to a flat smooth work surface of almost any composition, horizontal or vertical or at an angle in between, for use in removing and replacing needle shields. The suction cup is advantageous because, unlike magnetic attachments, it does not require a ferro-magnetic surface.

Figure 8:
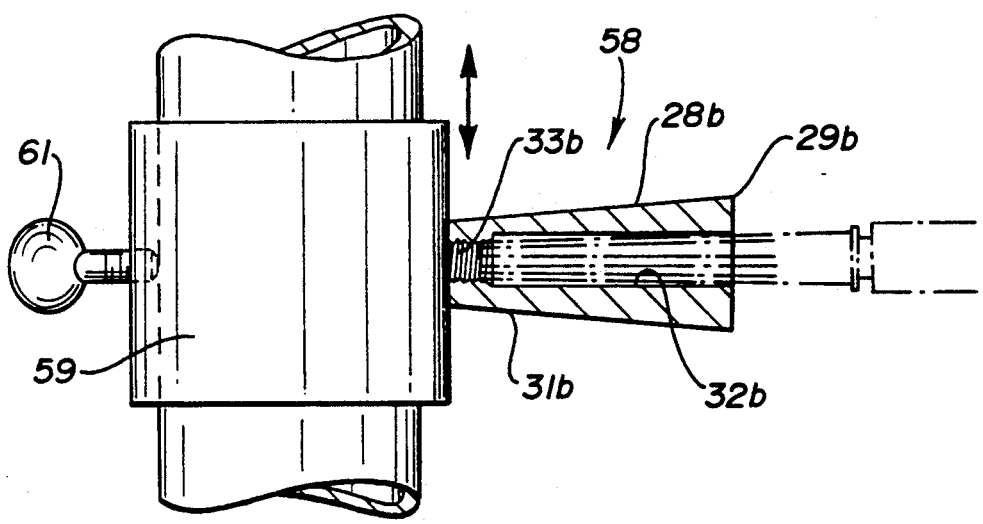
FIG. 8 is another alternative embodiment of the present invention including a movable adjustable collar for positioning the device along the length of a pole or rod.

Referring now to FIG. 8 another alternative embodiment of a device 58 for the removal and replacement of a needle shield includes a housing 28b having a proximal end 29b and a distal end 31b. The housing includes a bore 32b therein beginning at the proximal end. Screw threads 33b are included in the housing along the bore and accessible through the bore. The screw threads are capable of engaging and holding the outside surface of the needle shield which is placed into the bore through the proximal end of the housing and rotated in a direction to advance the needle shield distally along the thread. Stabilizing means is included at the distal end of the housing in the form of cylindrical collar 59. Collar 59 can be placed over a cylindrical support such as the vertical pole member of an I.V. pole. Collar 59 is fixedly attached to the housing so that the housing may be moved up and down the I.V. pole or to any desired angular position to suit the user and removably held in that position using thumb screw 61. Syringes are frequently used in I.V. additive programs wherein medication is injected through a pierceable septum into an I.V. set. The need for safe needle shield removal and replacement in I.V. therapy can be satisfied by the present embodiment of the present invention which allows incorporation of the invention with an I.V. pole and provides substantial adjustment with respect to height and angle to accommodate the user preference. It is within the purview of the instant invention to include other types of clamps such as clamps for attaching the device to a horizontal work surface or a door or a drawer wall and the clamp illustrated herein is representative of those many possibilities.

Figure 9:
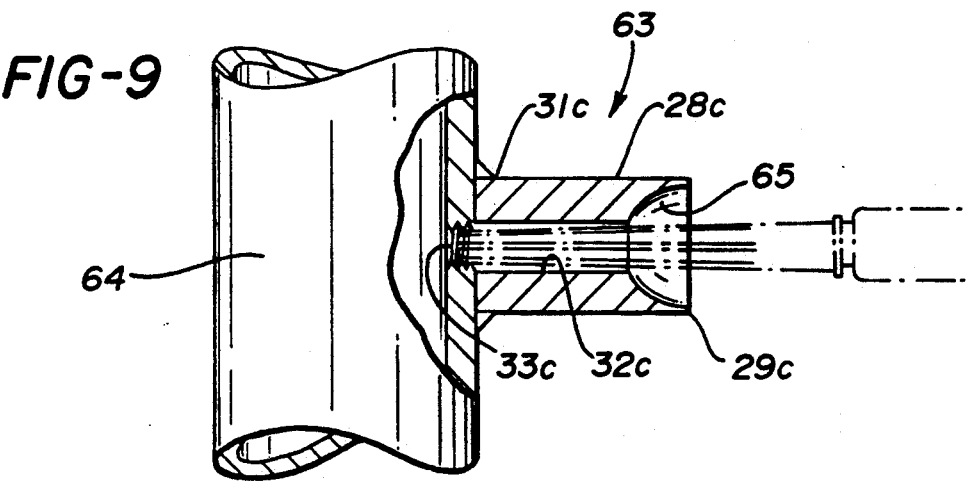
FIG. 9 is another alternative embodiment illustrating the device of the present invention formed integrally with a pole or rod.

FIG. 9 illustrates still another alternative embodiment of a device 63 for the removal and replacement of a needle shield. This embodiment includes a housing 28c having a proximal end 29c and a distal end 31c. The housing includes a bore 32c beginning at the proximal end. Screw threads 33c in the housing along the bore are accessible through the bore. The screw threads are capable of engaging and holding the outside surface of the needle shield. A stabilizing means is provided in the form of a structural fixture such as, a vertical I.V. pole or other structure such as the frame of a nursing cart. Stabilizing means in this embodiment is in the form of I.V. pole 64 which positions the housing and holds the housing so that the user can remove and replace needle shields using a one-handed procedure. In this embodiment, the threads are part of the I.V. pole. The present embodiment also includes guide means for directing the distal end of the needle shield toward the bore. In this embodiment the guide means includes a concave surface 65.

Figure 10:
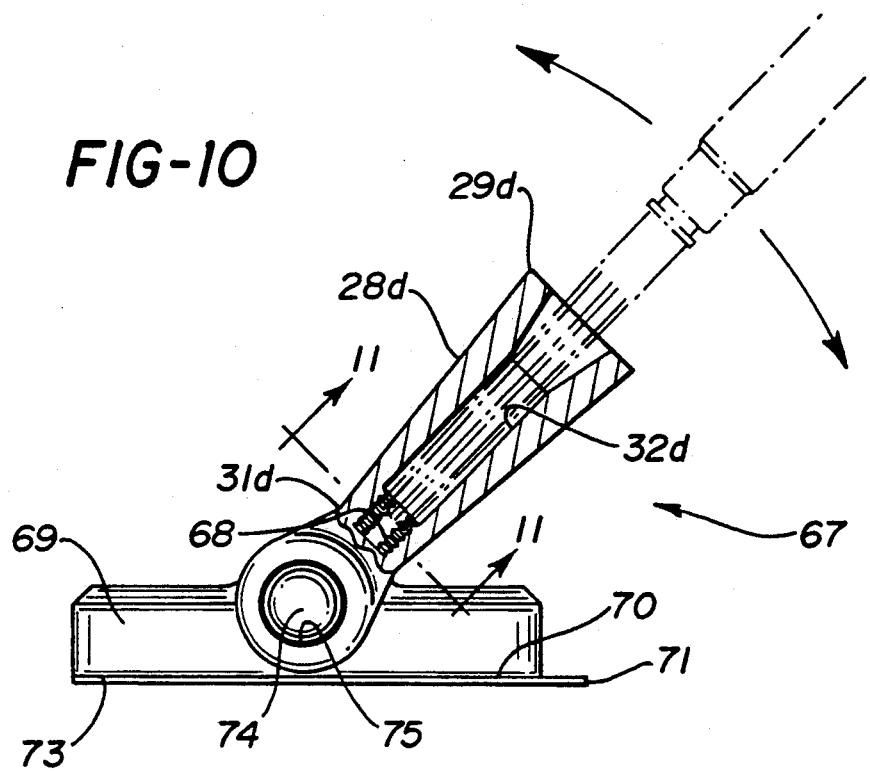
FIG. 10 is another alternative embodiment of the present invention providing for angular movement of the device with respect to the work surface.
Figure 11:
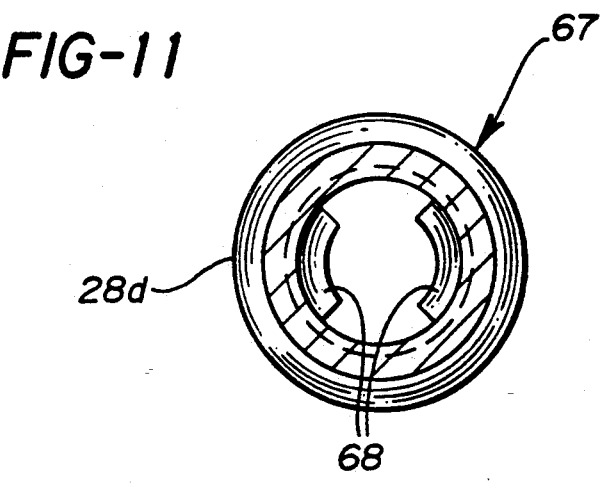
FIG. 11 is an enlarged cross-sectional view of the device of FIG. 10 taken along line 11—11.

FIGS. 10 and 11 illustrate still another alternative embodiment of a device for the removal and replacement of a needle shield. The device includes a proximal end 29d and a distal end 31d. The housing includes a bore 32d beginning at the proximal end. Intermittent screw threads 68 in the housing along bore 32d are capable of engaging and holding the outside surface of a needle shield which is placed into the bore through proximal end 29d. Threads in this embodiment are intermittent, non-continuous, rather than continuous and are intended to be more aggressive and to cut into or deform the surface of the needle shield in the manner of a self-tapping thread.

Stabilizing means in the form of mounting base 69 is provided at the distal end of the housing for positioning and holding the housing and for allowing a person to remove and replace the needle shield without touching the device. Mounting base 69 also includes adhesive 70 and release sheet 71 on its bottom surface 73. In this embodiment the device may be attached to a smooth work surface by removing release sheet 71 and placing the adhesive coated surface of the mounting base on the work surface to attach the mounting base thereto.

Device 67 also includes hinge 74 projecting from mounting base 69 into aperture 75 of the housing for allowing the manual adjustment of the angular relationship between the housing and the mounting base. The hinge structure of the present embodiment allows the user to orient the housing at a convenient angle for comfortable needle shield removal and replacement and also allows the user to compensate for the angle of the surface to which the mounting base is attached.

The housing of the present invention may be constructed of a wide variety of rigid materials with materials which are harder than the needle shield being removed and replaced being desirable. Materials such as aluminum and stainless steel being preferred along with plastics of equal or greater hardness than the needle shield. The housing may also be made of a thermoplastic material, which are harder or softer than the needle shield being removed and replaced, with a metal insert for the thread structure or a metallic plating or coating over the material which forms the the threads. The thread size being determined by the size of the needle shields being retained. A thread of approximately 0.25 inch diameter, having approximately 28 threads per inch is suitable for many commercially available needle shields. Housings attached to I.V. structural poles or metal collars can be made of metal and welded to the poles or collars or made of a wide variety of materials and attached using an adhesive which is suitable for the materials in question.

Thus it can be seen that the present invention provides a simple, straight-forward, reliable, easily fabricated device for the removal and replacement of a needle shield which holds the needle shield in a releasably secure position without relying on axially applied frictional forces to engage the needle shield in the device.

What is claimed is:

1. A device for the removal and replacement of a needle shield having a distal end, an open proximal end and a side wall therebetween having an outside surface comprising:

a housing having a proximal end and a distal end, said housing having a bore therein beginning at said proximal end;

thread means in said housing along said bore and accessible through said bore, said thread means for engaging and holding the outside surface of the needle shield which is placed into said bore through said proximal end of said housing and rotated in a direction to advance the needle shield distally along said thread means, wherein at least the portion of said thread means for engaging the needle shield is made of metal; and stabilizing means at said distal end of said housing for positioning and holding said housing for allowing a person to remove and replace a needle shield without touching said device.

2. The device for removal and replacement of a needle shield of claim 1 further including a first portion of said bore between said proximal end of said housing and said thread means.

3. The device for removal and replacement of a needle shield of claim 1 further including guide means for directing the distal end of a needle shield toward said bore.

4. The device for removal and replacement of a needle shield of claim 3 wherein said guide means includes a concave surface at said proximal end of said housing surrounding said bore.

5. The device for removal and replacement of a needle shield of claim 3 wherein said guide means includes a frusto-conically shaped surface at said proximal end of said housing surrounding said bore.

6. The device for removal and replacement of a needle shield of claim 1 wherein said thread means includes a right handed thread.

7. The device for removal and replacement of a needle shield of claim 1 wherein said stabilizing means includes adhesive means for allowing said device to be attached to a work surface.

8. The device for removal and replacement of a needle shield of claim 1 wherein said stabilizing means includes suction cup means for allowing said device to be removably attached to a smooth flat work surface.

9. The device for removal and replacement of a needle shield of claim 1 wherein said stabilizing means includes a magnet for allowing said device to be removably attached to a ferro-magnetic work surface.

10. The device for removal and replacement of a needle shields of claim 1 wherein said stabilizing means includes clamp means for allowing said device to be attached to a work surface.

11. The device for removal and replacement of a needle shield of claim 1 wherein said stabilizing means includes clamp means for allowing said device to be attached to a cylindrical pole.

12. The device for removal and replacement of a needle shield of claim 1 wherein said stabilizing means includes a vertically oriented pole.

13. The device for removal and replacement of a needle shield of claim 1 further including hinge means between said housing and said stabilizing means for allowing the manual adjustment of the angular relationship of said housing with respect to said stabilizing means.

14. A device for the removal and replacement of a needle shield having a distal end, an open proximal end and a side wall therebetween having an outside surface comprising:
    a housing having a proximal end and a distal end, said housing having a bore therein beginning at said proximal end;
    thread means in said housing along said bore and accessible through said bore, said thread means being spaced from said proximal end of said housing, said thread means for engaging and holding the outside surface of the needle shield which is placed into said bore through said proximal end of said housing and rotated in a direction to advance the needle shield distally along said thread means, wherein at least the portion of said thread means for engaging the needle shield is made of metal.

15. A device for the removal and replacement of a needle shield having a distal end, an open proximal end and a side wall therebetween having an outside surface comprising:
    a housing having a proximal end and a distal end, said housing having a bore therein beginning at said proximal end;
    thread means in said housing along said bore and accessible through said bore, said thread means being spaced from said proximal end of said housing by a first portion of said bore between said proximal end of said housing and said thread means, said thread means including a right hand thread, said thread means being capable of engaging and holding the outside surface of the needle shield which is placed in said bore through said proximal end of said housing and rotated in a clockwise direction, wherein at least the portion of said thread means for engaging the needle shield is made of metal;
    guide means for directing the distal end of a needle shield toward said bore; and
    stabilizing means at said distal end of said housing for positioning and holding said housing for allowing a person to remove and replace a needle shield without touching said device.

16. A device for the removal and replacement of a needle shield having a distal end, an open proximal end and a side wall therebetween having an outside surface comprising:
    a housing have a proximal end and a distal end, said housing having a bore therein beginning at said proximal end;
    thread means in said housing along said bore and accessible through said bore, said thread means for engaging and holding the outside surface of the needle shield which is placed into said bore through said proximal end of said housing and rotated in a direction to advance the needle shield distally along said thread means, wherein said thread means includes an intermittent non-continuous thread; and
    stabilizing means at said distal end of said housing for positioning and holding said housing for allowing a person to remove and replace a needle shield without touching said device.

17. A device for the removal and replacement of a needle shield having a distal end, an open proximal end and a side wall therebetween having a outside surface comprising:
    a housing having a proximal end and a distal end, said housing having a bore therein beginning at said proximal end;
    thread means in said housing along said bore and accessible through said bore, said thread means being spaced from said proximal end of said housing by a first portion of said bore between said proximal end of said housing and said thread means, said thread means including a right hand thread, said thread including an intermittent non-continuous thread; said thread means being capable of engaging and holding the outside surface of the needle shield which is placed in said bore through said proximal end of said housing and rotated in a clockwise direction;
    guide means for directing the distal end of a needle shield toward said bore; and
    stabilizing means at said distal end of said housing for positioning and holding said housing for allowing a person to remove and replace a needle shield without touching said device.

* * * * *